(12) United States Patent
Cheng et al.

(10) Patent No.: US 8,475,939 B2
(45) Date of Patent: Jul. 2, 2013

(54) M-TERPHENYL COMPOUND DERIVATIVES AND APPLICATION FOR ORGANIC LIGHT EMITTING DIODE

(75) Inventors: Chien-Hong Cheng, Hsinchu (TW); Cheng-An Wu, Hsinchu (TW); Fang-Iy Wu, Hsinchu (TW); Cheng-Hung Shih, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 111 days.

(21) Appl. No.: 12/985,678

(22) Filed: Jan. 6, 2011

(65) Prior Publication Data

US 2011/0220880 A1    Sep. 15, 2011

(30) Foreign Application Priority Data

Dec. 3, 2010  (TW) .............................. 99142097 A

(51) Int. Cl.
*H01L 51/54* (2006.01)

(52) U.S. Cl.
USPC ........... 428/690; 428/917; 313/504; 313/505; 313/506; 257/40; 257/E51.032; 257/E51.026; 257/E51.05; 546/18; 546/79; 546/81; 546/101; 548/440

(58) Field of Classification Search
USPC ........... 428/690, 917; 313/504, 505; 544/234; 548/440; 546/18, 79, 81, 101; 257/40, E51.032, 257/E51.026, E51.05
See application file for complete search history.

(56) References Cited

U.S. PATENT DOCUMENTS

| | | | | |
|---|---|---|---|---|
| 5,932,362 A | * | 8/1999 | Nagai et al. | 428/690 |
| 2003/0137239 A1 | * | 7/2003 | Matsuura et al. | 313/503 |
| 2005/0208331 A1 | * | 9/2005 | Maeda | 428/690 |

FOREIGN PATENT DOCUMENTS

| | | | |
|---|---|---|---|
| JP | 2004-253298 | * | 9/2004 |
| JP | 2007-243101 | * | 9/2007 |

*Primary Examiner* — Jennifer Chriss
*Assistant Examiner* — Gregory Clark
(74) *Attorney, Agent, or Firm* — Muncy, Geissler, Olds & Lowe, PLLC

(57) ABSTRACT

An m-terphenyl derivative has a structure of formula (I) or (II):

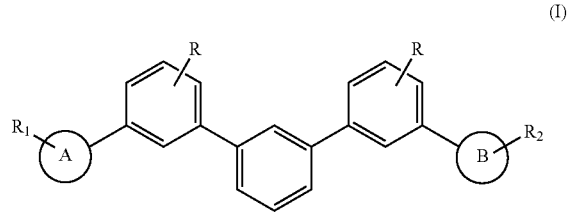

(I)

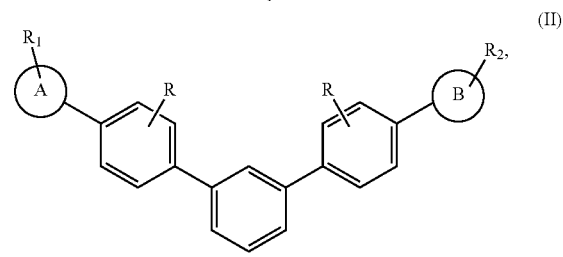

(II)

wherein A and B are five-membered heterocyclic compounds selected from the group consisting of pyrrole, pyrazole, imidazole, 1,2,3-triazole, 1,2,4-triazole, 1,2,3,4-tetrazole, 1,2-thiazole, 1,3-thiazole and 1,3,4-thiadiazole, each of substituents R, $R_1$ and $R_2$ is a member independently selected from the group consisting of H, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl. The compound of the present invention may have advantages in good electron affinity, low HOMO and thereby achieving hole blocking and may be used for electron transport material and/or electron injection material.

14 Claims, 1 Drawing Sheet

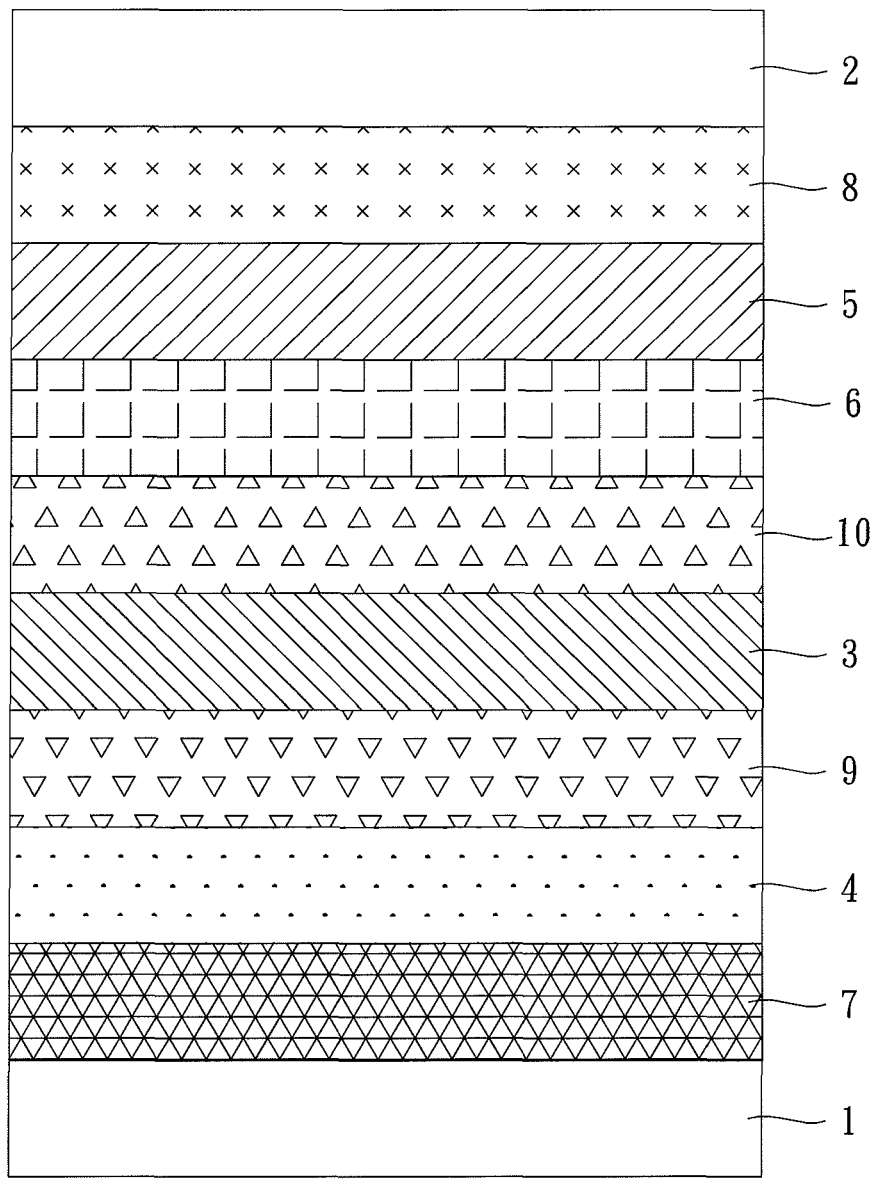

M-TERPHENYL COMPOUND DERIVATIVES AND APPLICATION FOR ORGANIC LIGHT EMITTING DIODE

BACKGROUND OF THE INVENTION

1. Field of the Invention

The present invention relates to a novel compound and organic light emitting diode using the same, particularly to m-terphenyl derivatives and organic light emitting diode using the same.

2. Description of the Prior Art

OLED works on the principal that electrons and holes diffuse through an electron transport layer (ETL) and hole transport layer (HTL), respectively, to enter a light-emitting layer, and recombine in the emitting region to form a particle generally referred as exciton. In order for the exciton to relax to the ground state, the energy is given off in the form of photo radiation. The radiation color can be tuned by applying different emitting materials. OLED has been highly-regarded due to a lot of advantages, such as self illumination, wider visual angle (>170°), shorter response time (~μs), higher contrast, higher efficiency, lower power consumption, higher brightness, lower operative voltage (3-10V), thinner size (<2 mm), flexibility and so on.

The exciton generated from recombining holes and electrons may have triplet state or singlet state for its spin state. The singlet exciton relaxation would radiate fluorescence, and the triplet exciton relaxation would radiate phosphorescence. Phosphorescence achieves 3-fold efficiency when compared to fluorescence and may greatly enhance the IQE (internal quantum efficiency) of devices up to 100% by adopting heavy metal in electroluminescent configuration to achieve strong spin-orbital coupling and mixing of singlets and triplets. Therefore, phosphorescent heavy metals are now adopted as phosphorescent dopants in the emitting layer of OLED. In addition, by applying a doping method on the emitting layer, self-quenching of the emitting materials can be reduced greatly to enhance the efficiency of the device.

However, due to the higher triplet energy level for phosphorescent molecules, some energy would tend to flow to other material with lower triplet energy level and cause illumination in the device. Therefore, A good electron transport material should include following properties: 1. reversible electrochemical redox properties; 2. suitable HOMO and LUMO values so as to provide lowered operating voltage for good electron injection and optional hole blocking properties, where the HOMO value for the known electron transport material with hole blocking property is usually more than 6 eV; 3. higher electron mobility so as to obtain the combination area departed from the cathode and increase the generation rate of excitons; 4. higher thermal stability so as to prevent the heat generated by driving device from shortening the life expectancy of devices; and 5. good film forming ability.

To sum up, it is an important issue to achieve balance between electrons and holes in the devices and provide devices with better performance; therefore, it is necessary and critical to develop a novel carrier transport material.

SUMMARY OF THE INVENTION

The present invention is directed to m-terphenyl derivatives and organic light emitting diode using the same.

According one embodiment, an m-terphenyl derivative having a structure of formula (I) or (II):

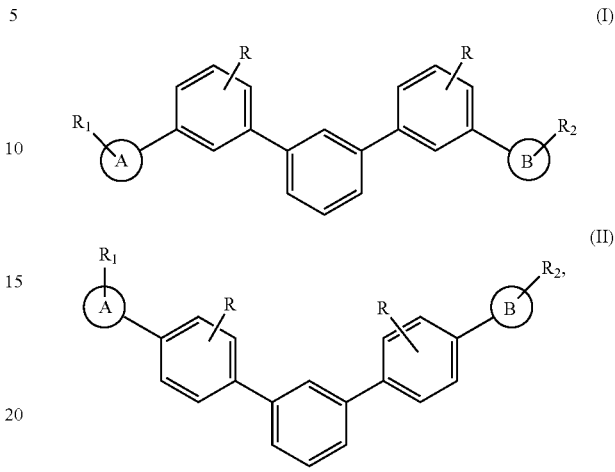

wherein A and B are five-membered heterocyclic compounds selected from the group consisting of pyrrole, pyrazole, imidazole, 1,2,3-triazole, 1,2,4-triazole, 1,2,3,4-tetrazole, 1,2-thiazole, 1,3-thiazole and 1,3,4-thiadiazole, each of substituents R, $R_1$ and $R_2$ is a member independently selected from the group consisting of H, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

According to another embodiment, an organic light emitting diode includes a cathode, an anode, an emitting layer and an organic material layer. The emitting layer is configured between the cathode and the anode. The organic material layer is configured between the emitting layer and the cathode and comprises the aforementioned m-terphenyl derivatives.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein:

FIG. 1 is a schematic diagram illustrating an OLED device containing m-terphenyl derivatives.

DESCRIPTION OF THE PREFERRED EMBODIMENT

The m-terphenyl derivatives of the present invention having a structure of formula (I) or (II) is provided.

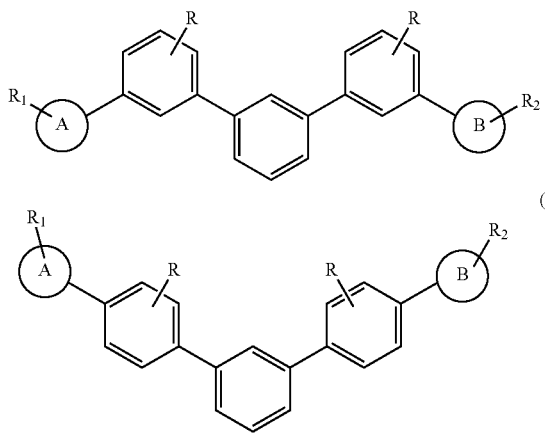

(I)

(II)

A and B may be the same or different five-membered heterocyclic compounds containing nitrogen, for example without limited to pyrrole, pyrazole, imidazole, 1,2,3-triazole, 1,2,4-triazole, 1,2,3,4-tetrazole, 1,2-oxazole, 1,3-oxazole, 1,3,4-oxadiazole, 1,2,4-oxadiazole, 1,2-thiazole, 1,3-thiazole or 1,3,4-thiadiazole. In addition, A and B may be bonded to the m-terphenyl via C or N atom.

Each of substituents R, $R_1$ in A and $R_2$ in B of the m-terphenyl derivatives is a member independently selected from the group consisting of H, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

The term "aryl" refers to a hydrocarbon moiety having one or more aromatic rings. Examples of aryl moieties include phenyl (Ph), phenylene, naphthyl, naphthylene, pyrenyl, anthryl, and phenanthryl.

The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other. In one preferred embodiment, The m-terphenyl derivatives of the present invention having a structure of formula (III) or (IV) is provided.

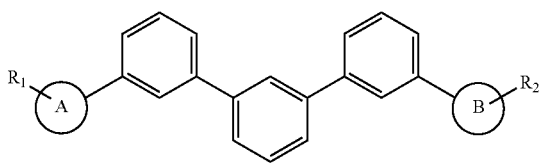

(III)

In one preferred embodiment, The m-terphenyl derivatives of the present invention having a structure of formula (III) or (IV) is provided.

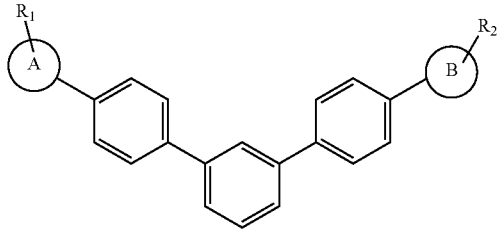

(III)

(IV)

In one preferred embodiment, A is the same as B and the substituent $R_1$ of A is the same as the substituent $R_2$ of B. A may be pyrrole, pyrazole, imidazole, 1,2,3-triazole, 1,2,4-triazole or 1,2,3,4-tetrazole. For example, the compound 1,2,4-triazole have been characterized in having good electron affinity and ultra low HOMO (highest occupied molecular orbital) resulting in blocking the hole easily. Therefore, it is suitable and efficient to adopt 1,2,4-triazole in m-terphenyl core for electron transporting material.

In one embodiment, m-terphenyl derivatives having heterocyclic substituents are represented as formulae (a) to (e).

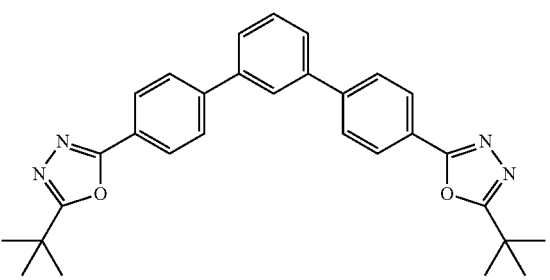

(a)

(b)
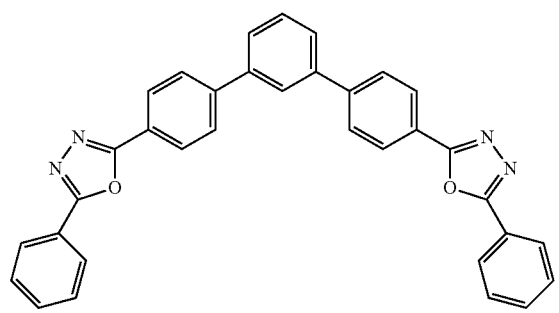
(c)
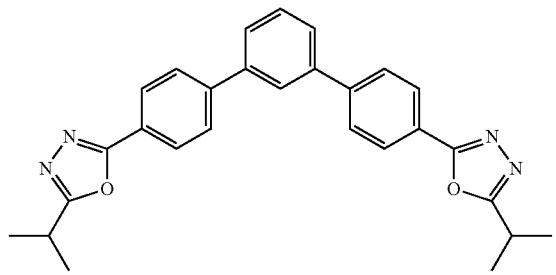
(d)
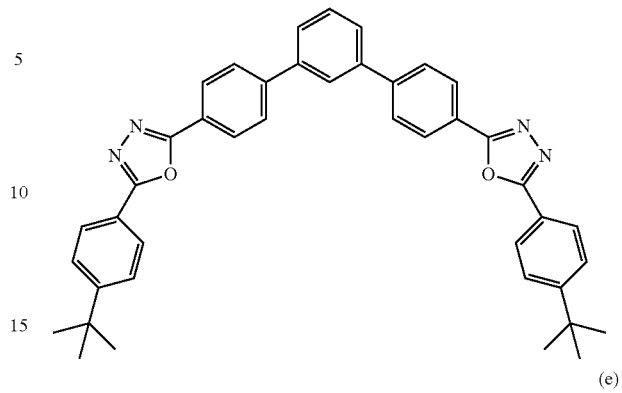
(e)
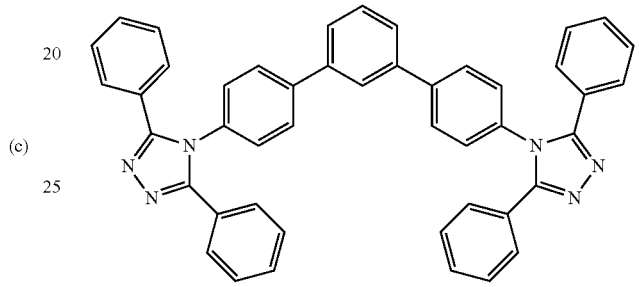
In another embodiment, m-terphenyl derivatives having heterocyclic substituents are represented as formulae (f) to (j).
(f)
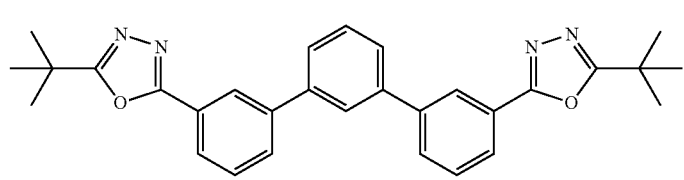
(g)
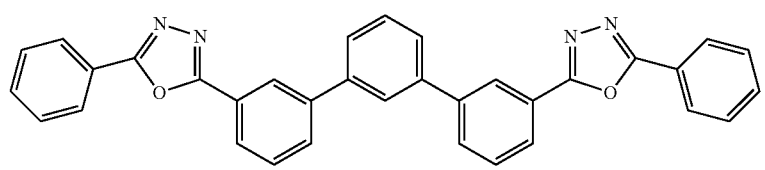
(h)
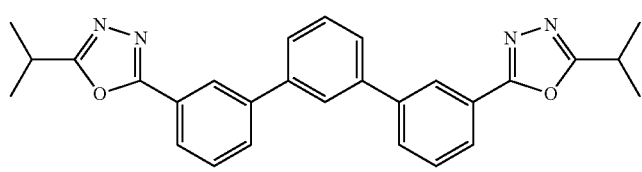
(i)
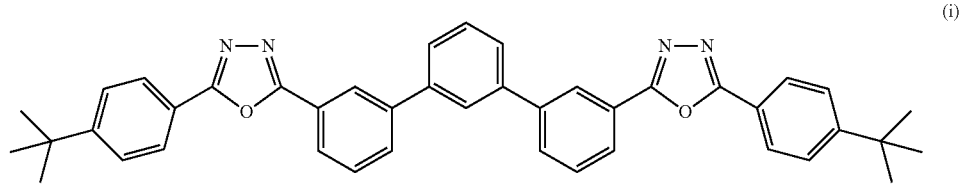

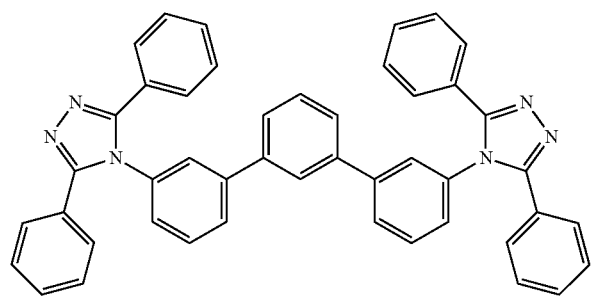

Refer to FIG. 1, which is a schematic diagram illustrating an organic light emitting device containing m-terphenyl derivatives according to one embodiment of the present invention. The light emitting device includes an emitting layer 3 configured between the anode 1 and cathode 2. The emitting layer 3 is made of host emitting material doped with light emitting material. The light emitting device may also include a hole injecting layer 7, a hole transport layer 4, an electron blocking layer 9, an emitting layer 3, an exciton blocking layer 10, a hole blocking layer 6, an electron transport layer 5 and an electron injecting layer 8 sequentially configured on top of the anode 1. The real thickness of each layer doesn't correspond to the schematic size, and exciton blocking layer 10, electron blocking layer 9, hole blocking layer 6 and electron injecting layer 8 may be optional. The m-terphenyl derivatives having heterocyclic substituents may function as an electron transport material, an electron injection material, a hole blocking material or an exciton blocking material.

Compound Synthesis

Refer to following description illustrating the synthetic pathway of the m-terphenyl derivatives of the present invention.

Compound m-2a, Bis(1,3,4-oxadiazole-5-diyl)3,3'-m-terphenyl, for example, may be obtained from the reaction of reactants m-1a 2-(3-bromophenyl)-1,3,4-oxadiazole and 1,3-bis(4,4,5,5-tetramethyl-1,3,2-dioxaborolan-2-yl)benzene in the presence of $K_2CO_3$ and $PdCl_2(PPh_3)_2$.

Accordingly, compound p-2a, Bis(1,3,4-oxadiazole-5-diyl) 4,4'-m-terphenyl, for example, was obtained from the reaction of reactants 2-(4-bromophenyl)-1,3,4-oxadiazole and 1,3-bis(4,4,5,5-tetramethyl-1,3,2-dioxaborolan-2-yl)benzene in the presence of $K_2CO_3$ and $PdCl_2(PPh_3)_2$.

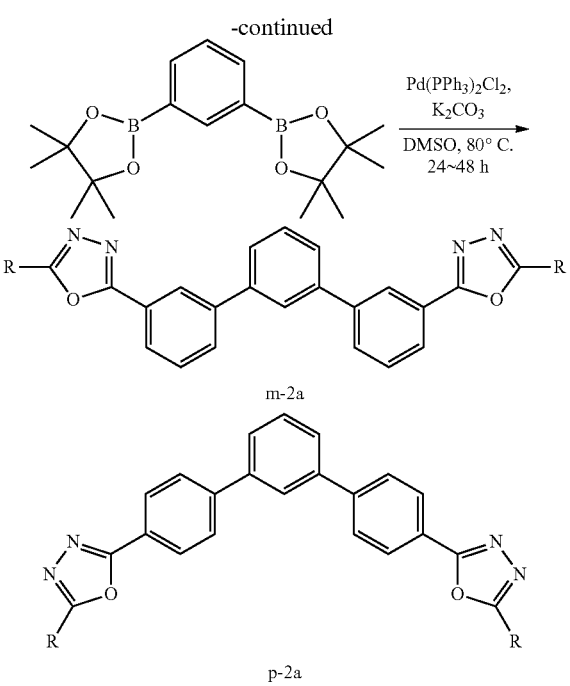

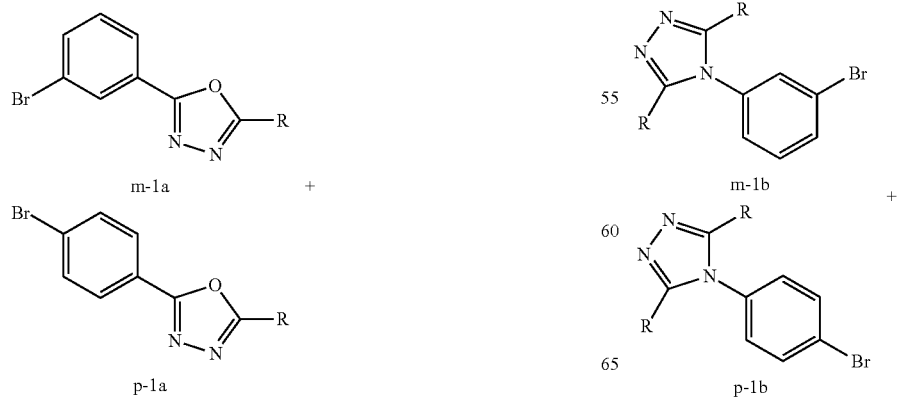

Therefore, referring to following reaction formulae, products m-2b, p-2b, m-2c or p-2c may be obtained by choosing various starting materials m-1b, p-1b, m-1c or p-1c for reaction.

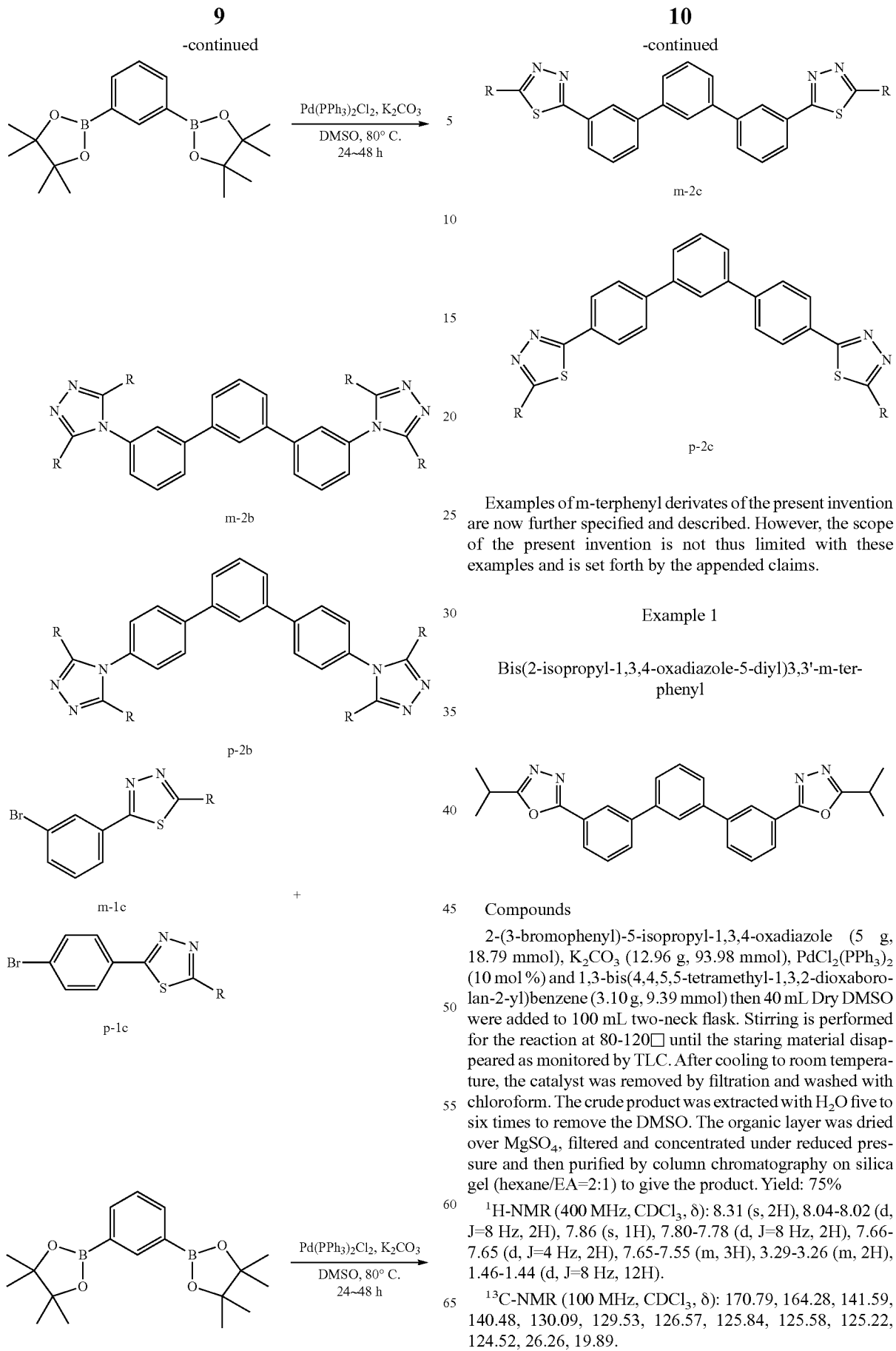

Examples of m-terphenyl derivates of the present invention are now further specified and described. However, the scope of the present invention is not thus limited with these examples and is set forth by the appended claims.

Example 1

Bis(2-isopropyl-1,3,4-oxadiazole-5-diyl)3,3'-m-terphenyl

Compounds 2-(3-bromophenyl)-5-isopropyl-1,3,4-oxadiazole (5 g, 18.79 mmol), $K_2CO_3$ (12.96 g, 93.98 mmol), $PdCl_2(PPh_3)_2$ (10 mol %) and 1,3-bis(4,4,5,5-tetramethyl-1,3,2-dioxaborolan-2-yl)benzene (3.10 g, 9.39 mmol) then 40 mL Dry DMSO were added to 100 mL two-neck flask. Stirring is performed for the reaction at 80-120□ until the staring material disappeared as monitored by TLC. After cooling to room temperature, the catalyst was removed by filtration and washed with chloroform. The crude product was extracted with $H_2O$ five to six times to remove the DMSO. The organic layer was dried over $MgSO_4$, filtered and concentrated under reduced pressure and then purified by column chromatography on silica gel (hexane/EA=2:1) to give the product. Yield: 75%

$^1$H-NMR (400 MHz, $CDCl_3$, δ): 8.31 (s, 2H), 8.04-8.02 (d, J=8 Hz, 2H), 7.86 (s, 1H), 7.80-7.78 (d, J=8 Hz, 2H), 7.66-7.65 (d, J=4 Hz, 2H), 7.65-7.55 (m, 3H), 3.29-3.26 (m, 2H), 1.46-1.44 (d, J=8 Hz, 12H).

$^{13}$C-NMR (100 MHz, $CDCl_3$, δ): 170.79, 164.28, 141.59, 140.48, 130.09, 129.53, 126.57, 125.84, 125.58, 125.22, 124.52, 26.26, 19.89.

HRMS (EI) Calcd for $C_{28}H_{26}N_4O_2$ (M$^+$): 450.2056. Found: 450.2060.

Example 2

Bis(2-isopropyl-1,3,4-oxadiazole-5-diyl)4,4'-m-terphenyl

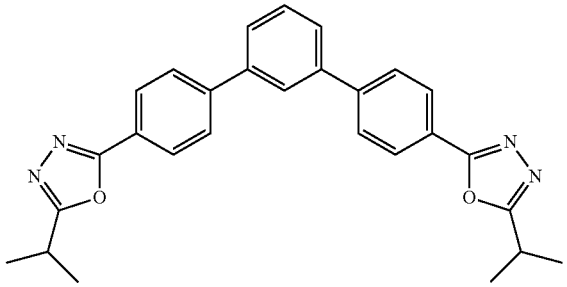 [SMILES: CC(C)c1nnc(-c2ccc(-c3cccc(-c4ccc(-c5nnc(C(C)C)o5)cc4)c3)cc2)o1]

Compounds 2-(3-bromophenyl)-5-isopropyl-1,3,4-oxadiazole (5 g, 18.79 mmol), $K_2CO_3$ (12.96 g, 93.98 mmol), $PdCl_2(PPh_3)_2$ (10 mol %) and 1,3-bis(4,4,5,5-tetramethyl-1,3,2-dioxaborolan-2-yl)benzene (3.10 g, 9.39 mmol) then 40 mL Dry DMSO were added to a 100 mL two-neck flask. The product was then obtained according to those steps in example 1. Yield: 82%

$^1$H-NMR (400 MHz, CDCl$_3$, δ): 8.13-8.11 (d, J=8 Hz, 4H), 7.85 (s, 1H), 7.77-7.75 (d, J=8 Hz, 4H), 7.66-7.64 (d, J=8 Hz, 2H), 7.58-7.55 (m, 1H), 3.29-3.26 (m, 2H), 1.47-1.45 (d, J=8 Hz, 12H).

$^{13}$C-NMR (100 MHz, CDCl$_3$, δ): 170.88, 164.34, 143.78, 140.63, 129.56, 127.66, 127.25, 126.84, 125.39, 123.17, 26.42, 20.03.

HRMS (EI) Calcd for $C_{28}H_{26}N_4O_2$ (M$^+$): 450.2056. Found: 450.2058.

Example 3

Bis(2-tert-butyl-1,3,4-oxadiazole-5-diyl)3,3'-m-terphenyl

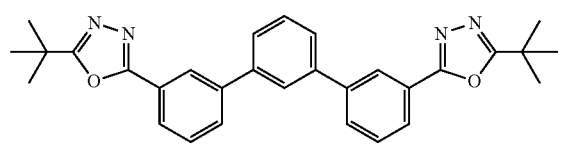 [SMILES: CC(C)(C)c1nnc(-c2cccc(-c3cccc(-c4cccc(-c5nnc(C(C)(C)C)o5)c4)c3)c2)o1]

Compounds 2-(3-bromophenyl)-5-tert-butyl-1,3,4-oxadiazole (5 g, 17.85 mmol), $K_2CO_3$ (12.31 g, 89.27 mmol), $PdCl_2(PPh_3)_2$ (10 mol %) and 1,3-bis(4,4,5,5-tetramethyl-1,3,2-dioxaborolan-2-yl)benzene (2.94 g, 8.92 mmol) then 40 mL Dry DMSO were added to a 100 mL two-neck flask. The product was then obtained according to those steps in example 1. Yield: 78%.

$^1$H-NMR (400 MHz, CDCl$_3$, δ): 8.29 (s, 2H), 8.04-8.02 (d, J=8 Hz, 2H), 7.86 (s, 1H), 7.80-7.78 (d, J=8 Hz, 2H), 7.67-7.65 (d, J=8 Hz, 2H), 7.61-7.57 (m, 3H), 1.48 (s, 18H).

$^{13}$C-NMR (100 MHz, CDCl$_3$, δ): 173.31, 164.53, 141.89, 140.85, 130.34, 129.54, 126.86, 126.20, 125.85, 125.52, 124.87, 32.54, 28.28.

HRMS (FAB) Calcd for $C_{30}H_{30}N_4O_2$ (M$^+$+1): 479.2447. Found: 479.2457.

Example 4

Bis(2-tert-butyl-1,3,4-oxadiazole-5-diyl)4,4'-m-terphenyl

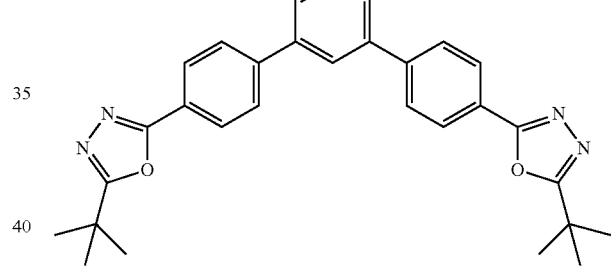

Compounds 2-(4-bromophenyl)-5-tert-butyl-1,3,4-oxadiazole (5 g, 17.85 mmol), $K_2CO_3$ (12.31 g, 89.27 mmol), $PdCl_2(PPh_3)_2$ (10 mol %) and 1,3-bis(4,4,5,5-tetramethyl-1,3,2-dioxaborolan-2-yl)benzene (2.94 g, 8.92 mmol) then 40 mL Dry DMSO were added to a 100 mL two-neck flask. The product was then obtained according to those steps in example 1. Yield: 86%

$^1$H-NMR (400 MHz, CDCl$_3$, δ): 8.15-8.13 (d, J=8 Hz, 4H), 7.87 (s, 1H), 7.79-7.77 (d, J=8 Hz, 4H), 7.68-7.66 (d, J=8 Hz, 2H), 7.60-7.57 (m, 1H), 1.51 (s, 18H).

$^{13}$C-NMR (100 MHz, CDCl$_3$, δ): 173.19, 164.36, 143.78, 140.68, 129.57, 127.67, 127.28, 126.85, 125.96, 123.26, 32.48, 28.22.

HRMS (FAB) Calcd for $C_{30}H_{30}N_4O_2$ (M$^+$+1): 479.2447. Found: 479.2449. Anal. calcd. For $C_{30}H_{30}N_4O_2$: C, 75.29; H, 6.32; N, 11.71. Found: C, 75.18; H, 6.34; N, 11.50.

Example 5

Bis(2-(4-tert-butylphenyl)-1,3,4-oxadiazole-5-diyl)3,3'-m-terphenyl

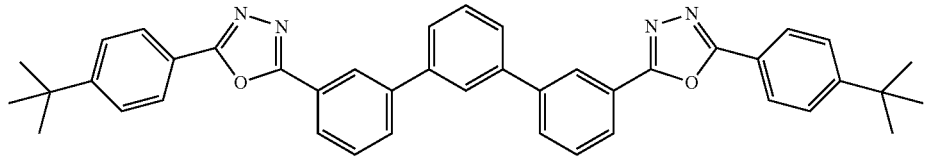 [SMILES: CC(C)(C)c1ccc(-c2nnc(-c3cccc(-c4cccc(-c5cccc(-c6nnc(-c7ccc(C(C)(C)C)cc7)o6)c5)c4)c3)o2)cc1]

Compounds 2-(3-bromophenyl)-5-(4-tert-butylphenyl)-1,3,4-oxadiazole (5 g, 14.04 mmol), $K_2CO_3$ (9.61 g, 70.20 mmol), $PdCl_2(PPh_3)_2$ (10 mol %) and 1,3-bis(4,4,5,5-tetramethyl-1,3,2-dioxaborolan-2-yl)benzene (2.31 g, 7.02 mmol) then 40 mL Dry DMSO were added to a 100 mL two-neck flask. The product was then obtained according to those steps in example 1. Yield: 76%

$^1$H-NMR (400 MHz, $CDCl_3$, δ): 8.41 (s, 2H), 8.14-8.12 (d, J=8 Hz, 2H), 8.09-8.07 (d, J=8 Hz, 4H), 7.92 (s, 1H), 7.84-7.82 (d, J=8 Hz, 2H), 7.68-7.66 (d, J=8 Hz, 2H), 7.64-7.53 (m, 7H), 1.34 (s, 18H).

$^{13}$C-NMR (100 MHz, $CDCl_3$, δ): 164.73, 164.21, 155.33, 141.81, 140.63, 130.36, 129.70, 129.58, 129.54, 126.76, 126.05, 125.99, 125.82, 125.52, 124.57, 120.94, 35.02, 31.04.

HRMS (EI) Calcd for $C_{42}H_{38}N_4O_2$ (M$^+$): 630.2995. Found: 630.2995.

Example 6

Bis(2-(4-tert-butylphenyl)-1,3,4-oxadiazole-5-diyl)4,4'-m-terphenyl

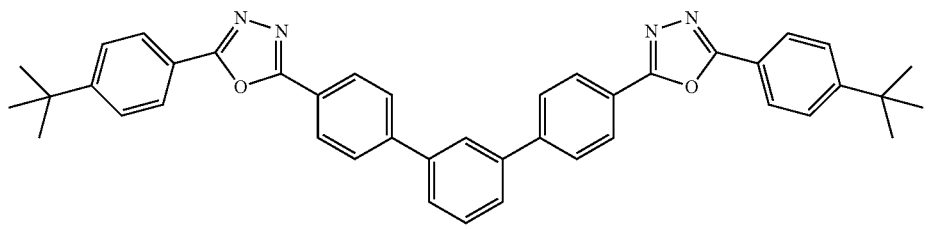 [SMILES: CC(C)(C)c1ccc(-c2nnc(-c3ccc(-c4cccc(-c5ccc(-c6nnc(-c7ccc(C(C)(C)C)cc7)o6)cc5)c4)cc3)o2)cc1]

Compounds 2-(4-bromophenyl)-5-(4-tert-butylphenyl)-1,3,4-oxadiazole (5 g, 14.04 mmol), $K_2CO_3$ (9.61 g, 70.20 mmol), $PdCl_2(PPh_3)_2$ (10 mol %) and 1,3-bis(4,4,5,5-tetramethyl-1,3,2-dioxaborolan-2-yl)benzene (2.31 g, 7.02 mmol) then 40 mL Dry DMSO were added to a 100 mL two-neck flask. The product was then obtained according to those steps in example 1. Yield: 85%

$^1$H-NMR (400 MHz, $CDCl_3$, δ): 8.22-8.20 (d, J=8 Hz, 4H), 8.07-8.05 (d, J=8 Hz, 4H), 7.88 (s, 1H), 7.81-7.79 (d, J=8 Hz, 4H), 7.67-7.65 (d, J=8 Hz, 2H), 7.59-7.53 (m, 5H), 1.35 (s, 18H).

$^{13}$C-NMR (100 MHz, $CDCl_3$, δ): 164.66, 164.10, 155.33, 143.87, 140.58, 129.59, 127.72, 127.36, 126.86, 126.73, 126.00, 125.92, 123.03, 120.98, 35.03, 31.06.

HRMS (EI) Calcd for $C_{42}H_{38}N_4O_2$ (M$^+$): 630.2995. Found: 630.2999.

Example 7

Bis((3,5-diphenyl)-1,2,4-triazole-4-diyl)3,3'-m-terphenyl

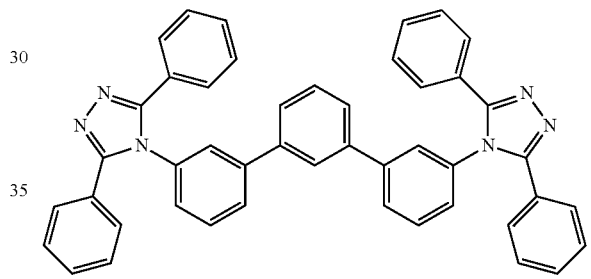

Compounds 4-(3-bromophenyl)-3,5-diphenyl-4H-1,2,4-triazole (5 g, 13.33 mmol), $K_2CO_3$ (9.2 g, 66.66 mmol), $PdCl_2(PPh_3)_2$ (10 mol %) and 1,3-bis(4,4,5,5-tetramethyl-1,3,2-dioxaborolan-2-yl)benzene (2.2 g, 6.6 mmol) then 40 mL Dry DMSO were added to a 100 mL two-neck flask. The product was then obtained according to those steps in example 1. Yield: 80%

$^1$H-NMR (400 MHz, $CDCl_3$, δ): 7.65-7.63 (m, 4H), 7.51-7.28 (m, 24H), 7.14-7.12 (m, 4H).

$^{13}$C-NMR (100 MHz, $CDCl_3$, δ): 154.62, 142.35, 139.76, 135.66, 130.28, 129.64, 128.83, 128.42, 128.04, 126.87, 126.68, 126.59, 126.17, 125.69.

HRMS (EI) Calcd for $C_{46}H_{32}N_6$ (M$^+$): 668.2688. Found: 668.2688.

Example 8

Bis((3,5-diphenyl)-1,2,4-triazole-4-diyl)4,3'-m-terphenyl

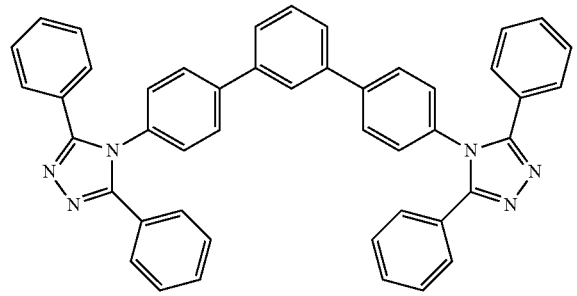 [SMILES: c1ccc(-c2nnc(-c3ccccc3)n2-c2ccc(-c3cccc(-c4ccc(-n5c(-c6ccccc6)nnc5-c5ccccc5)cc4)c3)cc2)cc1]

Compounds 4-(4-bromophenyl)-3,5-diphenyl-4H-1,2,4-triazole (5 g, 13.33 mmol), $K_2CO_3$ (9.2 g, 66.66 mmol), $PdCl_2(PPh_3)_2$ (10 mol %) and 1,3-bis(4,4,5,5-tetramethyl-1,3,2-dioxaborolan-2-yl)benzene (2.2 g, 6.6 mmol) then 40 mL Dry DMSO were added to a 100 mL two-neck flask. The product was then obtained according to those steps in example 1. Yield: 83%

$^1$H-NMR (400 MHz, $CDCl_3$, δ): 7.84 (s, 1H), 7.73-7.71 (d, J=8 Hz, 4H), 7.67-7.26 (m, 27H).

$^{13}$C-NMR (100 MHz, $CDCl_3$, δ): 154.76, 141.82, 140.00, 134.46, 129.66, 128.83, 128.44, 128.18, 126.58, 125.91.

HRMS (EI) Calcd for $C_{46}H_{32}N_6$ ($M^+$): 668.2688. Found: 668.2699.

Energy Level of Compounds

The LUMO, HOMO and energy level of compounds are listed in Table 1.

TABLE 1

Energy level of compounds

| Compound | LUMO (eV) | HOMO (eV) | energy level (eV) |
|---|---|---|---|
| Example 1 | −2.18 | −6.13 | 3.95 |
| Example 2 | −2.38 | −6.25 | 3.87 |
| Example 3 | −2.17 | −6.12 | 3.95 |
| Example 4 | −2.38 | −6.25 | 3.87 |
| Example 5 | −2.37 | −6.27 | 3.9 |
| Example 6 | −2.74 | −6.43 | 3.69 |
| OXD-7 (Reference)* | −2.53 | −6.34 | 3.81 |

*Reference compound OXD-7 (1,3-Bis[(p-tert-butyl)phenyl-1,3,4-oxadiazoyl]benzene) is used for electron transport material.

Triplet Energy State of Compounds

TABLE 1

Triplet energy level of compounds

| Compound | $E_T$ (eV) |
|---|---|
| Example 1 | 2.83 eV |
| Example 2 | 2.56 eV |
| Example 3 | 2.83 eV |
| Example 4 | 2.56 eV |
| Example 5 | 2.9 eV |
| Example 6 | 2.77 eV |
| OXD-7 (Reference) | 2.70 eV |

In OLED devices, a higher energy level of triplet state of the electron transport materials would prevent the excitons in the devices from diffusing to the electron transport layer and lighting therein as well as undesired light leakage, thereby increasing light purity and lighting efficiency for the devices.

The triplet level of example compounds 1~6 of the present invention ranges from 2.77~2.9 eV, which is higher than that of OXD-7 (2.70 eV); therefore, the example compounds of the present invention would have better performance and be suitable for exciton blocking material.

Examples for OLED Structure

As for the formed device structure, ITO is used for the substrate and an electrode; the tested electrode includes LiF/Al; the tested emitting material includes Bis(4,6-difluorophenylpyridinato-N,C2)picolinatoiridium (Firpic), Iridium, fac-tris(2-phenylpyridine) iridium(III) (Ir(ppy)$_3$) and Bis(1-phenylisoquinoline)(acetylacetonate) iridium (III) (Ir(piq)$_2$acac); the tested electron transfer material includes Bhen(4,7-diphenyl-1,10-phenanthrolin) and Alq$_3$(tris(8-hydroxyquinoline)aluminum(III)), which also can be used for hole blocking material, or hole blocking material and electron transporting material simultaneously. The tested hole transporting material includes NPB (4,4'-bis[N-(1-naphthyl)-N-phenyl-amino]biphenyl) and TAPC (1,1'-bis(di-4-tolylaminophenyl)cyclohexane), which also can be used for electron blocking material, or electron blocking material and hole transporting material simultaneously. The m-2a and m-2b of the present invention may be used for electron transport material and/or electron injection material.

The detailed configuration and width (nm) of the tested devices are respectively illustrated as follows, where blue OLED devices include devices A, B, E; green OLED devices includes devices C, D; red OLED device includes device G; device G represents an OLED device with doping material; and the reference device adopts OXD-7 as the electron transport material.

Device A: NPB (50)/TAPC (15)/11% Firpic: host(40)/m-2b (12.5)/BPhen (12.5)/LiF (1)/Al (100).

Device B: NPB (50)/TAPC (15)/11% Firpic: host(40)/m-2a (12.5)/BPhen (12.5)/LiF (1)/Al (100).

Reference for Device A B (Ref-A,B): NPB (50)/TAPC (15)/11% Firpic: host (40)/OXD-7 (12.5)/Bphen (12.5)/LiF (1)/Al (100).

Device C: NPB (50)/TAPC (15)/5% Ir(PPy)$_3$: host (40)/m-2b (12.5)/TAZ (12.5)/LiF (1)/Al (100).

Device D: NPB (20)/TAPC (15)/16% Ir(ppy)$_3$: host (40)/m-2b (12.5)/TAZ (12.5)/LiF (1)/Al (100).

Reference for Device C D (Ref-C,D): NPB (20)/TAPC (15)/16% Ir(ppy)$_3$: host(40) OXD-7 (12.5)/TAZ (12.5)/LiF (1)/Al (100).

Device E: TAPC (30)/host 11% Firpic: mcp (50)/m-2b (30)/LiF (1)/Al (100).

Reference for Device E (Ref-E): TAPC (30)/host mcp: 11% Firpic (50)/OXD-7 (30)/LiF (1)/Al (100).

Device F: TAPC (50)/host: 10% Ir(piq)$_2$acac (50)/m-2a (30)/LiF (1)/Al (100).

Reference for Device F (Ref-F): TAPC (50)/host: 10% Ir(piq)$_2$acac (50)/OXD-7 (30)/LiF (1)/Al (100).

Device G: TAPC (30)/host Firpic: m-2 (50)/m-2a (30)/LiF (1)/Al (100)

The lighting performance of the test devices are listed in Table 3.

TABLE 3

Performance Comparison for OLED devices

| Device | $V_d{}^a$ | $L_{max}{}^b$ (Cd/m$^2$) | $\eta_{ext}{}^c$ (%) | $\eta_c{}^d$ (Cd/A) | $\eta_p{}^e$ (lm/W) | $\lambda_{max}{}^f$ | CIE@8 V |
|---|---|---|---|---|---|---|---|
| A | 4.0 | 18508 | 15.7 | 16.36 | 6.92 | 471 | (0.14, 0.29) |
| B | 4.1 | 23671 | 20.8 | 21.43 | 11.99 | 472 | (0.16, 0.35) |
| Ref-A, B | 4.1 | 13371 | 10 | 10.7 | 3.5 | 472 | (0.14, 0.34) |
| C | 3.6 | 7002 | 13.3 | 14.65 | 13.16 | 512 | (0.27, 0.60) |
| D | 2.5 | 71029 | 29.5 | 51.94 | 54.47 | 515 | (0.28, 0.63) |
| Ref-C, D | 6.84 | 16193 | 8.74 | 8.2 | 2.66 | 514 | (0.27, 0.62) |
| E | 4.3 | 50283 | 21 | 40.62 | 28.29 | 472 | (0.16, 0.32) |
| Ref-E | 3.61 | 14427 | 11.6 | 12 | 5.82 | 472 | (0.24, 0.35) |
| F | 3.34 | 7843 | 12.6 | 9.99 | 7.85 | 625 | (0.68, 0.32) |
| Ref-F | 3.57 | 4416 | 10.4 | 8.1 | 2.4 | 632 | (0.63, 0.32) |
| G | 5.84 | 2178 | 6.62 | 6.9 | 2.2 | 472 | (0.16, 0.34) |

$^a V_d$: drive voltage;
$^b L_{max}$: maximum luminescence;
$^c \eta_{ext}$: maximum external quantum efficiency;
$^d \eta_c$: maximum current efficiency;
$^e \eta_p$: maximum power efficiency;
$^f \lambda_{max}$: maximum emission wavelength.

Referring to Table 3, devices containing m-terphenyl derivative m-2a, m-2b of the present invention, in comparison to the reference device, are better in each index and have better performance.

To sum up, the m-terphenyl derivatives of the present invention have advantages in good electron drawing, low HOMO and achieving hole blocking and may be used for electron transport material and/or electron injection material.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. An m-terphenyl derivative having a structure of formula (I) or (II):

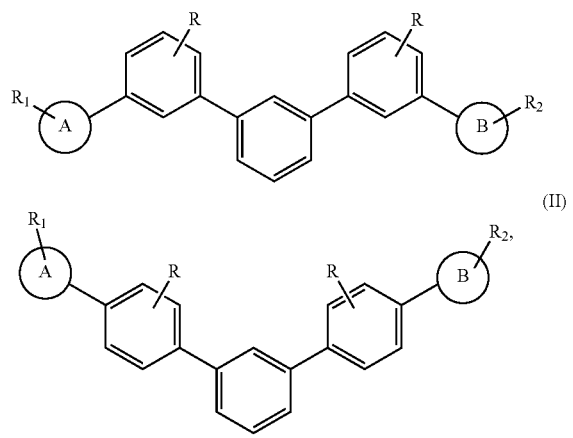

wherein A and B are five-membered heterocyclic compounds selected from the group consisting of pyrrole, pyrazole, imidazole, 1,2,3-triazole, 1,2,4-triazole, 1,2,3,4-tetrazole, 1,2-thiazole, 1,3-thiazole and 1,3,4-thiadiazole, A and B are bonded to the m-terphenyl via N atom, each of substituents R, R$_1$ and R$_2$ is a member independently selected from the group consisting of H, halo, cyano, trifluoromethyl, amino, C$_1$-C$_{10}$ alkyl, C$_2$-C$_{10}$ alkenyl, C$_2$-C$_{10}$ alkynyl, C$_3$-C$_{20}$ cycloalkyl, C$_3$-C$_{20}$ cycloalkenyl, C$_1$-C$_{20}$ heterocycloalkyl, C$_1$-C$_{20}$ heterocycloalkenyl, aryl and heteroaryl.

2. The m-terphenyl derivative as claimed in claim 1, wherein the five-membered heterocyclic compounds A and B are 1,2,4-triazole.

3. The m-terphenyl derivative as claimed in claim 1, wherein the five-membered heterocyclic compounds A and B are the same, and the substituents R$_1$ and R$_2$ are the same.

4. The m-terphenyl derivative as claimed in claim 1, having a structure of formulae (e) and (j):

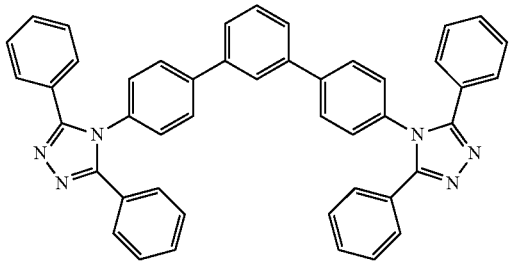
(e)

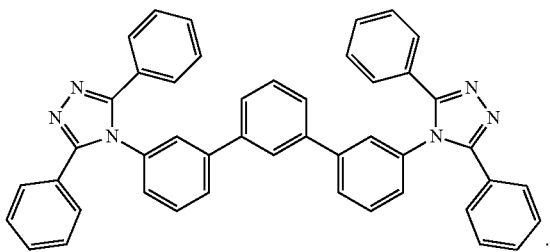
(j)

5. An organic light emitting diode, comprising:
a cathode;
an anode;
an emitting layer configured between the cathode and the anode; and
an organic material layer configured between the emitting layer and the cathode, wherein the organic material layer comprises an m-terphenyl derivative having a structure of formula (I) or (II):

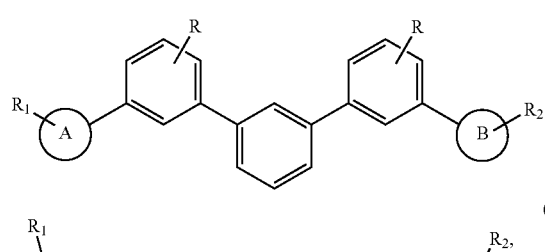
(I)

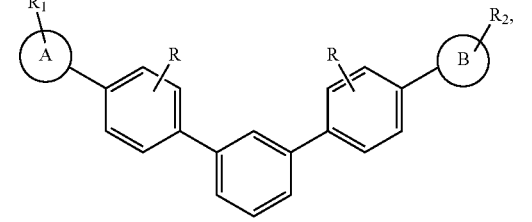
(II)

wherein A and B are five-membered heterocyclic compounds selected from the group consisting of pyrrole, pyrazole, imidazole, 1,2,3-triazole, 1,2,4-triazole, 1,2,3,4-tetrazole, 1,2-thiazole, 1,3-thiazole and 1,3,4-thiadiazole, A and B are bonded to the m-terphenyl via N atom, each of substituents R, $R_1$ and $R_2$ is a member independently selected from the group consisting of H, halo, cyano, trifluoromethyl, amino, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl and heteroaryl.

6. The organic light emitting diode as claimed in claim 5, wherein the five-membered heterocyclic compounds A and B are 1,2,4-triazole.

7. The organic light emitting diode as claimed in claim 5, wherein the five-membered heterocyclic compounds A and B are the same, and the substituents $R_1$ and $R_2$ are the same.

8. The organic light emitting diode as claimed in claim 5, wherein the m-terphenyl derivative has a structure of formulae (e) and (j):

9. The organic light emitting diode as claimed in claim 5, wherein the organic light emitting diode is a blue OLED, a green OLED, a red OLED, a blue phosphorescent OLED, a green phosphorescent OLED or a red phosphorescent OLED.

10. The organic light emitting diode as claimed in claim 5, wherein the organic material layer is an electron transport layer, and the m-terphenyl derivative is an electron transport material.

11. The organic light emitting diode as claimed in claim 5, wherein the organic material layer is an electron injection layer, and the m-terphenyl derivative is an electron injection material.

12. The organic light emitting diode as claimed in claim 5, wherein the organic material layer is a hole blocking layer, and the m-terphenyl derivative is a hole blocking material.

13. The organic light emitting diode as claimed in claim 5, wherein the organic material layer is an exciton blocking layer, and the m-terphenyl derivative is an exciton blocking material.

14. The m-terphenyl derivative as claimed in claim 1, wherein m-terphenyl derivative having a structure of formula (III) or (IV)

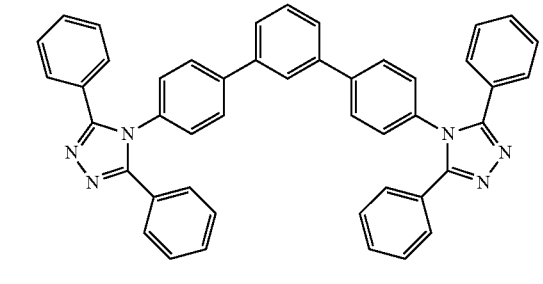

\* \* \* \* \*